(12) United States Patent
Malenke et al.

(10) Patent No.: US 8,708,002 B2
(45) Date of Patent: Apr. 29, 2014

(54) METHOD AND APPARATUS FOR VOLUMETRIC METERING AND DEPOSITING

(75) Inventors: Mark E. Malenke, Sun Prairie, WI (US); Charles Robert Sample, Green Bay, WI (US); Brian Charles Adamski, Pulaski, WI (US); Brian Wayne Tomac, DePere, WI (US); David Hess, Green Bay, WI (US); Tod Wesley Heleniak, Green Bay, WI (US)

(73) Assignee: Kraft Foods Group Brands LLC, Northfield, IL (US)

( * ) Notice: Subject to any disclaimer, the term of this patent is extended or adjusted under 35 U.S.C. 154(b) by 700 days.

(21) Appl. No.: 12/883,507

(22) Filed: Sep. 16, 2010

(65) Prior Publication Data
US 2012/0067451 A1    Mar. 22, 2012

(51) Int. Cl.
*B65B 1/04*     (2006.01)
*B65G 47/26*    (2006.01)
*A61M 5/178*    (2006.01)
*B65G 47/22*    (2006.01)

(52) U.S. Cl.
CPC ............. *A61M 5/1782* (2013.01); *B65G 47/22* (2013.01)
USPC ................. 141/2; 141/129; 141/280; 198/456

(58) Field of Classification Search
USPC ............................ 141/1, 2, 129, 280; 198/456
See application file for complete search history.

(56) References Cited

U.S. PATENT DOCUMENTS

| | | | |
|---|---|---|---|
| 782,772 A | 2/1905 | Bivert | |
| 1,077,162 A | 10/1913 | Rodakowski | |
| 1,339,486 A | 5/1920 | Stuart | |
| 1,512,331 A | 10/1924 | Funck | |
| 2,376,651 A | 5/1945 | Bardet | |
| 2,623,676 A | 12/1952 | Baker et al. | |
| 2,662,665 A | 12/1953 | Harper | |
| 3,154,117 A * | 10/1964 | Florin | 141/144 |
| 3,487,508 A * | 1/1970 | Baumgartner et al. | 425/219 |
| 3,581,677 A | 6/1971 | Strong | |
| 3,621,891 A | 11/1971 | Eisenberg | |
| 3,621,981 A | 11/1971 | Nimmo, Jr. et al. | |
| 4,152,976 A * | 5/1979 | Kawasaki et al. | 99/450.1 |
| 4,248,173 A * | 2/1981 | Kuhlman | 118/20 |
| 4,509,568 A * | 4/1985 | Kawaguchi et al. | 141/129 |
| 4,690,269 A | 9/1987 | Takao | |
| 4,865,092 A * | 9/1989 | Reichelt | 141/280 |
| 5,363,887 A * | 11/1994 | Haeberli | 141/12 |
| 5,404,919 A * | 4/1995 | Felts et al. | 141/80 |
| 5,523,101 A * | 6/1996 | Fitch, Jr. | 426/289 |
| 5,529,095 A * | 6/1996 | Felts et al. | 141/12 |
| 5,579,894 A | 12/1996 | Glazier et al. | |
| 6,672,343 B1 * | 1/2004 | Perret et al. | 141/95 |
| 6,837,281 B2 * | 1/2005 | Spiers et al. | 141/125 |

* cited by examiner

*Primary Examiner* — Timothy L Maust
(74) *Attorney, Agent, or Firm* — Fitch, Even, Tabin & Flannery LLP

(57) ABSTRACT

A method and apparatus are provided for the volumetric metering and depositing of a food product comprising a plurality of particles or flowable particles. The plurality of food particles are transported upon a discharge conveyor having a first rate of speed, the plurality of particles arranged uniformly from passing beneath a product leveling device. When the plurality of particles reach the end of the discharge conveyor, the particles fall from the end of the conveyor under the operation of gravity and are deposited in a shuttle while the shuttle travels at a second rate of speed from a position at least partially below the conveyor to collect the falling particles in cells or receiving receptacles. The relationship between the first rate of speed of the conveyor and the second rate of speed of the shuttle define a metered amount of particles collected in each of the receiving receptacles.

15 Claims, 7 Drawing Sheets

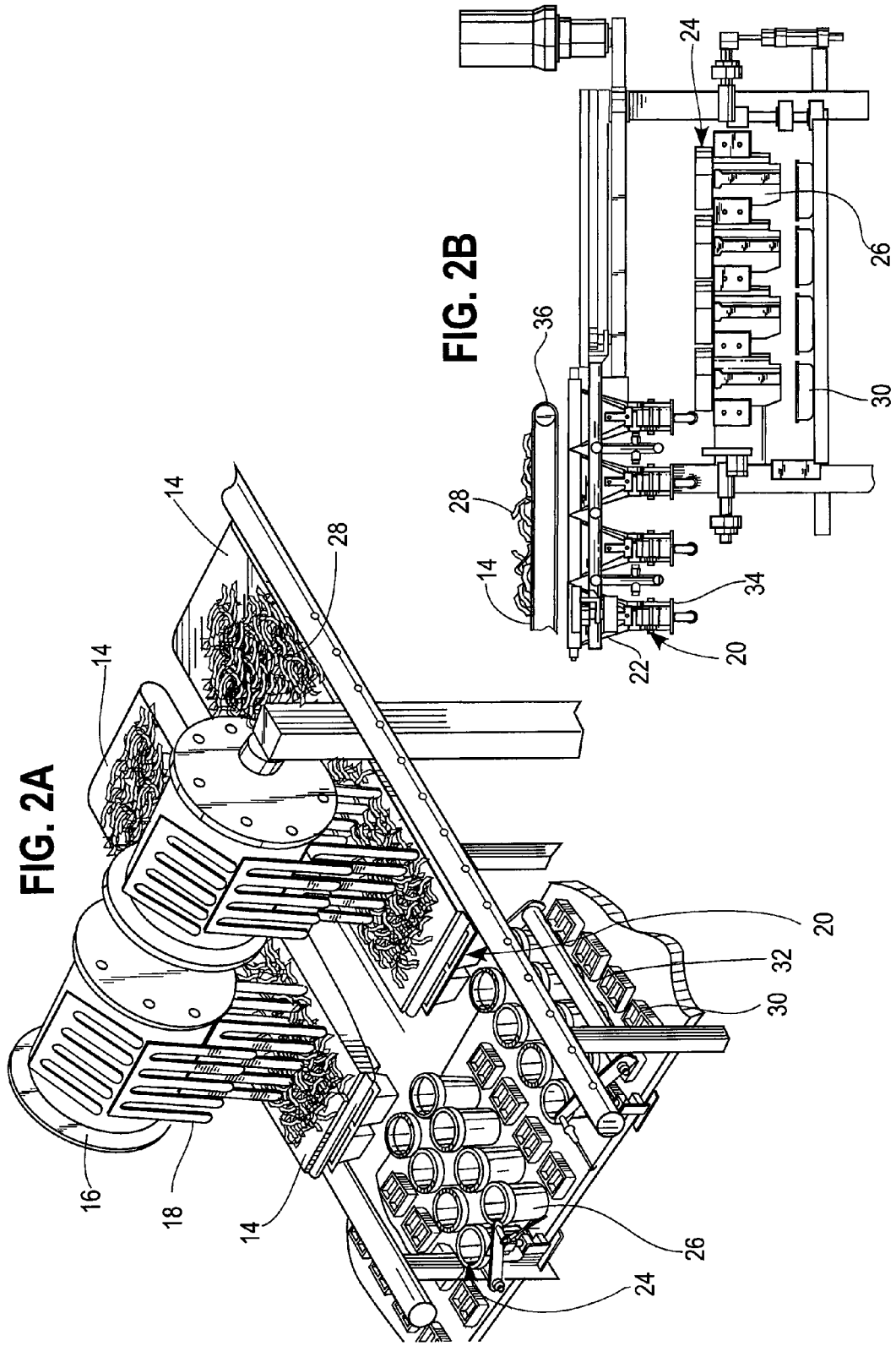

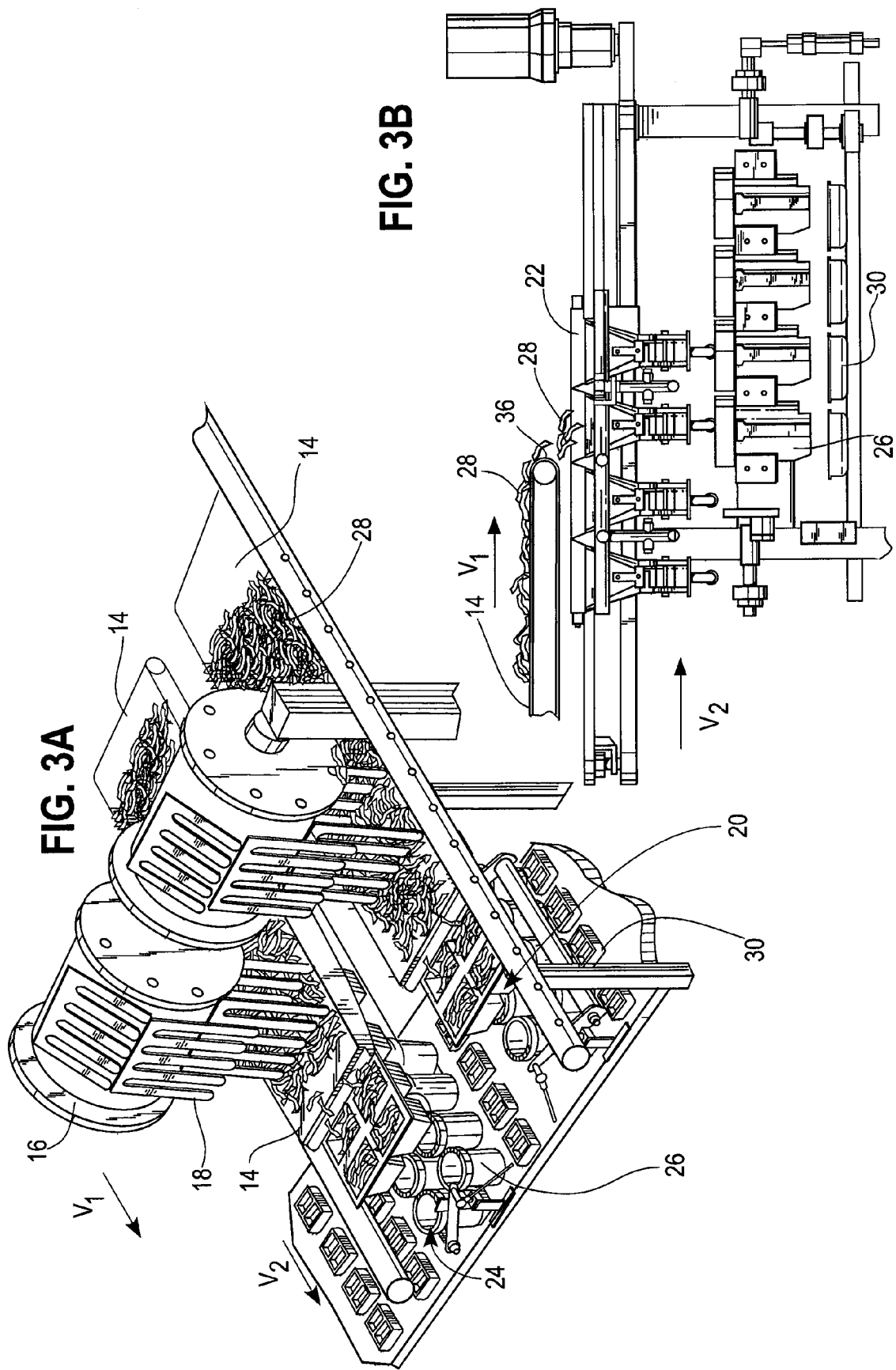

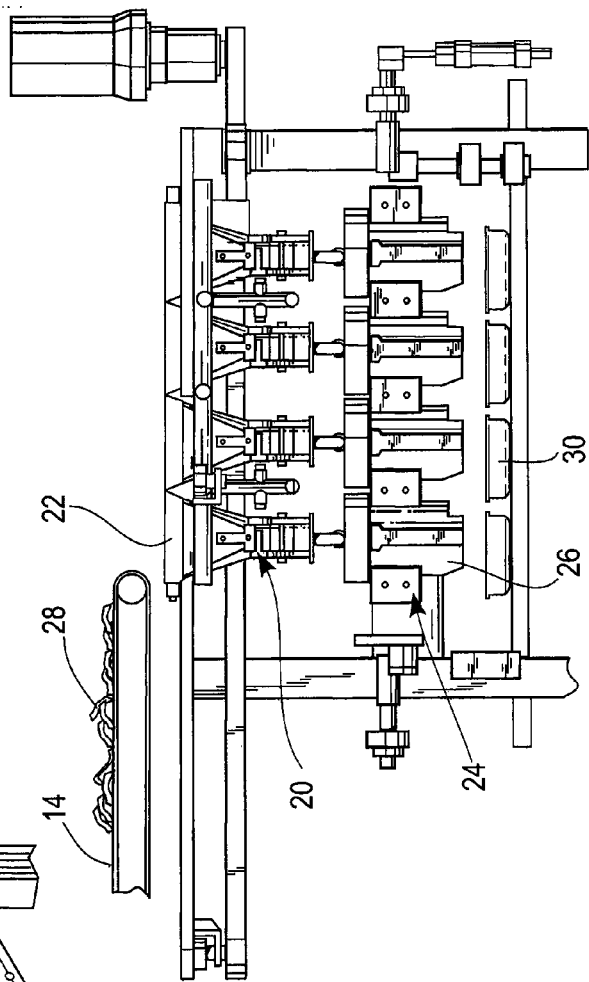
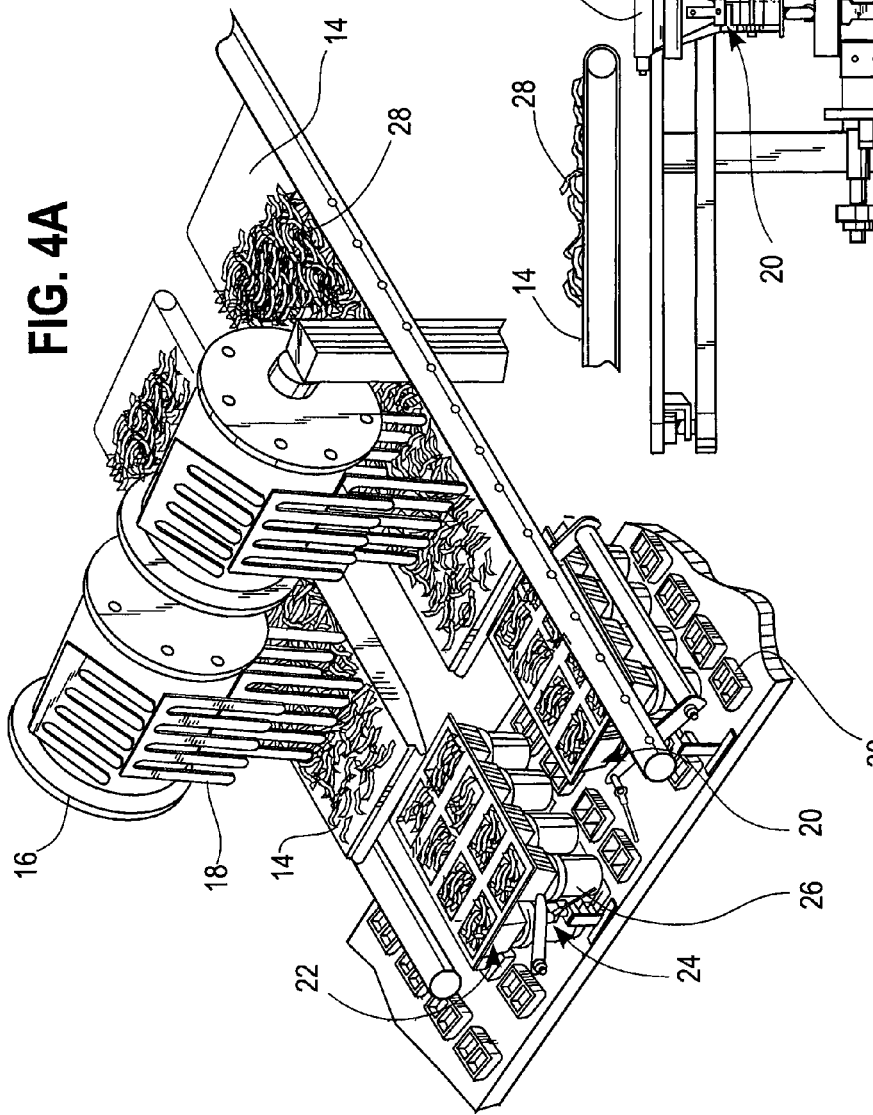

METHOD AND APPARATUS FOR VOLUMETRIC METERING AND DEPOSITING

FIELD

This application generally relates to a volumetric metering and depositing system and, in particular, a volumetric metering and depositing system that measures and deposits an item into a tray or other container.

BACKGROUND

One approach to metering and depositing of a food product, such as shredded cheese, in a tray is to shred the cheese in-line. This entails providing a whole or semi-whole block of cheese and shredding it into smaller pieces in-line while the process is running. However, this approach can be disadvantageous due to changing volumes of cheese over time when attempting to deposit the freshly shredded cheese into a tray or container and, in particular, a tray or container having multiple compartments. This can be due to the low bulk density value (which is defined as the mass/volume) of the product immediately after shredding, where the cheese shreds tend to retain their initial shape, i.e., length and width, just after shredding. However, over time, the newly shredded cheese can become more dense, which can result in the newly shredded cheese shrinking in size, i.e., having a smaller length and width. Therefore, if a newly shredded cheese product is relatively immediately deposited into a compartment of a package, over time what appeared to be a full cell can later appear to be only a partially filled cell due to the shrinking volume of the cheese.

Additionally, as the cheese block is shredded in-line, debris can fall from the cheese block or shredder into the process line such that the falling debris can contaminate the sealing surfaces of the tray lip or flange. When sealing the tray, the debris can interfere with forming a tight seal, such that leaking seals in the tray can result. Other issues can also arise, such as clogging of the shredders, which can cause a delay in shredding the cheese and consequently can cause process delays. The temperature of the cheese can vary, thus resulting in varying shred lengths due to the stiffness of the cheese, which can cause undesirable variations in the shredding quality. When the cheese is shredded it can have an arm press down on the opposite end of the cheese from the shredded end. The pressure provided by this arm can have different results based on the stiffness of the cheese. Thus, the in-line shredding system can exhibit poor control of the shredded cheese, resulting in inaccurate portion sizes. Additionally, the direct coupling of the shredding and assembly process can lead to assembly line inefficiencies. It can be challenging to shred small portion sizes, such as the cheese shreds, at the line speed because the fast line speeds can limit how efficiently the cheese block can be shredded. As the incoming cheese varies, the direct-coupled shredding process needs to be adjusted to compensate for that variation; those ongoing adjustments can be a continual source of line inefficiencies.

Transporting and depositing a plurality of products into a package can also be performed by transporting the products via a conveyor system into a container at the end of the conveyor. Where larger sized articles are being transferred to a tray or container, the items can easily be counted to determine the appropriate number of items needed per package. Where the articles are smaller in size and cannot be easily counted when transported on a conveyor, transferring a generally predetermined amount of the smaller sized articles becomes challenging, especially when the process is continuous or generally continuous in high speed commercial operations. Additionally, commercially available equipment can be physically too large for transporting and measuring small, numerous particles, and the equipment can have difficulties depositing small amounts of particles, such as less than about 1.5 oz., into a tray or package. In one approach, the container is stopped at the end of a conveyor to accurately collect the desired amount that has either been pre-measured prior to grouping the articles onto the conveyor, or has been weighed in the collection container after collection where the collection container can be equipped with a weighing/measuring device. In instances where the line or container is not stopped to collect the items, then the articles are dumped into the containers from the end of the conveyor line until the containers appear full or for a set time, without regard for the actual amount transferred. This can result in the containers having varying amounts of articles from container to container since the articles are being collected into the container without any way to control the weight or amount collected.

SUMMARY

A method of providing an automated process to volumetrically measure and deposit a plurality of particles, such as shredded cheese, or any other particles, into a container having one or multiple compartments. The plurality of particles are transported along a conveyor system that transfer the plurality of particles off of the end of the conveyor into a shuttle that accelerates from a position beneath the end of the conveyor to a position just past the end of the conveyor, collecting the particles as they fall under the operation of gravity from the end of the conveyor into the accelerating shuttle. The conveyor and the shuttle move at set rates of speed that are chosen to provide a set volume of particles collected within the plurality of receiving receptacles of the shuttle. This method allows for metered amounts of the particles to be deposited in the receptacles, such that the amount collected can be controlled and is repeatable.

In one aspect, the particles collected can be shredded cheese particles. A cheese block can be shredded off-line, using known methods, which gives the cheese shreds a more consistent bulk density value which can allow time for the cheese to equilibrate in size and volume, thus, avoiding some of the previously encountered process issues with shredding cheese in-line. Additionally, shredding the cheese off-line allows for the incorporation of anti-caking agents and other additives to enhance handling characteristics. Then, the previously cut and/or shredded cheese can be transported along the conveyor and deposited into a receiving receptacle of the shuttle, where the receiving receptacle can then deposit the cheese in-line into its respective tray or container for packaging the product.

When the shredded cheese is provided onto the conveyor belt, a raking system can be provided to distribute and spread out the cheese shreds evenly along the belt at a relatively consistent height of shreds. The raking system helps to ensure that the gaps between groups of cheese shreds are relatively consistent along the conveyor belt. The rakes and conveyor accept shredded cheese or other particles from, for example, another upstream conveyor such as a loading conveyor, and together deliver an accurate and repeatable mass flow of cheese to the receiving receptacles. As the cheese shreds are advanced to the end of the conveyor belt they fall off of the end of the belt. Underneath the belt can be provided a series of receiving receptacles that can be set in motion just prior to the shreds reaching the end of the conveyor. The receptacles travel along a horizontal plane, and as they are advanced from a first position at least partially beneath the conveyor belt to a second position past the end of the conveyor belt, they catch a certain amount of the cheese shreds as the shreds fall from the end of the belt and while the receiving receptacles are traveling at a set speed. The cheese-filled receiving receptacles deposit the cheese into their respective tray or compartment once the receiving receptacles reach the second position, which is above the containers. The rate of both the conveyor belt and the rate that the receiving receptacles are advanced determine the volume of cheese collected. This same process can be used for any type of food product, such as candies, nuts, etc. or any other type of non-food product, where a volume of product that cannot be counted or measured easily needs to be collected in-line and during operation of a continuous process.

BRIEF DESCRIPTION OF THE DRAWINGS

FIG. 2A is a perspective view of the system of FIG. 1 showing a product being transported on a conveyor;

FIG. 2B is a side view of the system shown in FIG. 2A;

FIG. 3A is a perspective view of the system of FIG. 2A beginning to fill a portion of a receiving receptacle with the product conveyed;

FIG. 3B is a side view of the system shown in FIG. 3A;

FIG. 4A is a perspective view of the system of FIG. 3A after the receiving receptacle has been completely filled with the product;

FIG. 4B is a side view of the system shown in FIG. 4A;

DETAILED DESCRIPTION

A method and apparatus for filling a compartment of a tray or container with a metered volume of a plurality of particles during an automated continuous process is described herein and provided in FIGS. 1-7. The automated process comprises volumetrically measuring and depositing the plurality of particles, such as shredded cheese, or any other particles, transferring the particles from the end of a conveyor into a shuttle having one or multiple receiving receptacles, the shuttle subsequently depositing the contents into a compartment of a tray for packaging the product therein.

The cheese shreds that are packaged typically have a length of about 0.75 to 1.25 inches, for example, which often can make it difficult to count the number of shreds. However, where a number of factors are satisfied, such as providing certain predetermined speeds of the conveyor and shuttle, a desired set volume of cheese shreds can be collected. In order to collect the desired volume of cheese shreds, the shreds can first be provided on a conveyor, the shreds having a predetermined height or thickness of cheese upon the conveyor, such that the shreds are relatively uniform in their spacing upon the conveyor. One method of accomplishing this can be by providing a raking assembly that utilizes fingers or rakes to evenly spread or distribute the cheese shreds. Alternatively, the layering and spreading of the product can also be done using a vibrating table or other feasible means based on the product that is being layered or separated. The next factor in ensuring a desired volume is collected is the speed of the conveyor interrelated with the speed of advancement or acceleration of the shuttle assembly. The two speeds are chosen such that the cheese shreds fall off of the end of the conveyor at an appropriate rate that allows a certain amount of shreds to fall into each individual receptacle of the shuttle assembly. The collected cheese shreds are then deposited into compartments of a tray and the process is repeated.

Figure 1:
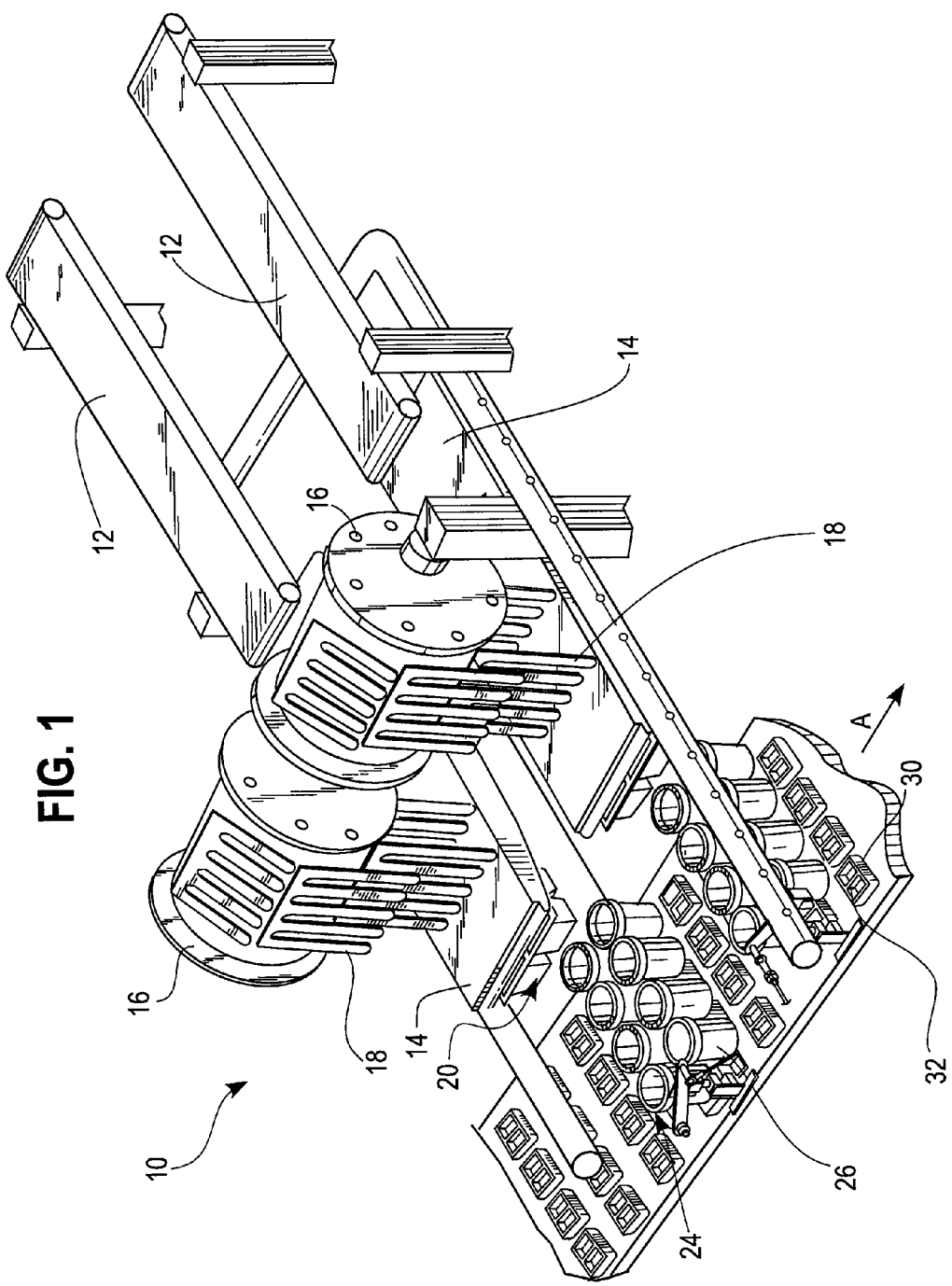
FIG. 1 is a perspective view of a volumetric metering and depositing system.
Figure 5:
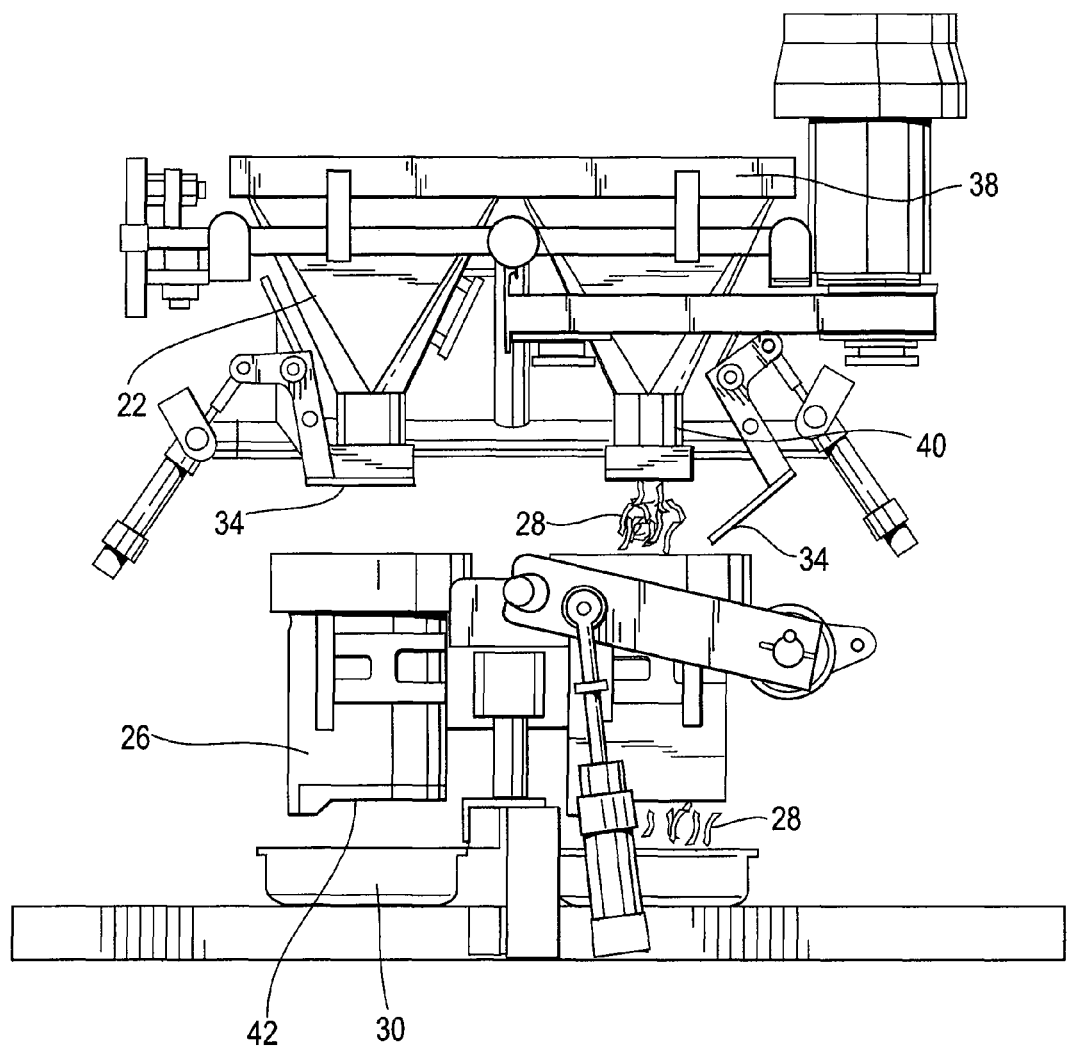
FIG. 5 is a side view of the receiving receptacle of FIG. 4B showing the product being deposited into a tray.

Turning to FIG. 1, a portioning assembly 10 is shown and, in particular, two portioning assemblies 10 are shown side by side. The portioning assembly 10 can be utilized with cheese shreds, as is shown in later figures, or with any other similar food or non-food particles that can be portioned and deposited into packages or trays. Although two portioning assemblies are shown side by side in the figures, a single portioning assembly can likewise be used or more than two assemblies can be used. The assembly 10 can comprise a loading conveyor 12 which transfers the loaded cheese shreds 28 (as shown in FIG. 2A) onto a second conveyor, such as a discharge conveyor 14. The discharge conveyor 14 can then pass the shreds 28 underneath a product leveling device, such as a raking system 16, to evenly distribute or spread the shreds 28 before transferring the shreds 28 off of the end 36 of the conveyor 14 under the operation of gravity (as in FIG. 3A) while the discharge conveyor 14 advances at a discharge speed or first rate of speed. The shuttle assembly 20 can advance at a shuttle speed or a second rate of speed. The first and second rates of speed are related to one another such that a metered volume or measured amount of cheese can be obtained based upon the two speeds chosen. There can be three steps involved in the movement of the conveyor and shuttle: an acceleration step, achieving the desired speed (i.e., either the first speed or the second speed), and a deceleration step. The metered volume can be a predetermined volume or a range of volumes. The shuttle assembly 20 can then further deposit the cheese shreds 28 into a funnel assembly 24, which can then deposit the cheese shreds 28 into respective compartments 32 of a tray 30 or other package or container. It is to be understood, that other food or non-food articles can be substituted for the cheese shreds 28 and that the portioning assembly 10 would function in a similar manner.

A loading conveyor 12 can optionally be provided as part of the portioning assembly 10 and, still optionally, two or more conveyors 12 in parallel can be provided. The loading conveyors 12 can provide a location to load or receive the pre-shredded cheese 28 and to transport it to the discharge conveyor 14 and the raking system 16. Where at least two loading conveyors 12 are provided, each can transport a different type of cheese or the same cheese. The pre-shredded cheese can be loaded onto the loading conveyor 12 either manually or from a hopper or other typical loading device. Optionally, the product can pass through a screen to prevent large cheese chunks from passing through the screen onto the conveyor 12, in an effort to keep the size of the cheese shreds 28 relatively uniform. In one aspect, a screen with an opening of about ½ inch can be provided, thus preventing cheese shreds larger in size than ½ inch to pass.

The cheese shreds 28 can be transported from the optional loading conveyors 12 directly onto the discharge conveyors 14. In another aspect, where the loading conveyors 12 are not provided, the cheese shreds 28 can be supplied directly onto the discharge conveyors 14 employing similar loading methods for the cheese as described above with respect to the loading conveyors 12. The discharge conveyors 14 can transport a plurality of food products, or cheese shreds 28, in a downstream direction toward a shuttle assembly 20 for receiving the cheese shreds 28, where the discharge conveyor 14 can travel at a first speed, or at a discharge speed. The discharge conveyor 14 can advance the cheese shreds 28 to the raking system 16, where rakes or fingers 18 can be provided positioned relative to the discharge conveyor 14 to distribute and organize the cheese shreds 28 relatively uniformly across the discharge conveyor 14 at a predetermined height and/or width, such that the shreds are distributed to have a uniform height and width or thickness of cheese after passing beneath a rake 18 upon the discharge conveyors 14. The predetermined height can include a range of heights that is appropriate for the product being portioned and deposited. Likewise, the predetermined width can include a range of widths that is appropriate for the product being portioned and deposited. The cheese shreds 28 can extend across a width of the discharge conveyor 14, where the width of the discharge conveyor 14 can be defined in a direction transverse to the downstream direction. The raking system 16 can level the cheese shreds 28 into a relatively uniform layer of stacked products and can also spread the cheese shreds 28 into a relatively uniform width extending transverse to the machine direction, spreading the cheese shreds 28 during the step of transporting them upon the discharge conveyor 14.

The post layering device product pile height can be adjustable by varying the gap between the layering device, or rake system 16, and discharge conveyor 14. The raking system 16 can be set to produce a height of about ¼ inch to about 1 inch thick of cheese. Additionally, a consistent pile height of cheese upstream of the rake 16 can help to maintain a consistent thickness of cheese on the discharge conveyor 14. Optionally, a sensor can be mounted upstream of the raking system 16 to monitor the pile or height of cheese and can command the corresponding loading conveyor 12 to automatically start or stop to maintain the desired height. The optional sensors can be configured to start and stop the loading conveyors 12 based on feedback from the sensors. In one aspect, the loading conveyors 12 can operate whenever the sensors indicate that additional cheese is needed based on a detection of no cheese.

The discharge conveyors 14 can run intermittently and can be synchronized with the shuttle assemblies 20. In one aspect, the surface speed of the conveyors 14 can be set at a first speed of about 8 to about 15 in/sec. The conveyor speed can be adjusted faster if the average portion weight of the cheese is too light or the conveyor speed can be adjusted slower if the average portion weight of the cheese is too heavy. Optionally, side guides can be provided to help maintain a consistent width of cheese on the conveyors 14 and can typically be spaced about 11 to about 11½ inches apart, for example. If desired, the discharge conveyors 14 can also comprise a cheese weight monitoring system, such as providing an additional conveyor support roller that can be mounted on load cells, for example.

Once the shredded cheese 28 reaches the end or edge 36 of the discharge conveyor 14, the cheese shreds 28 can fall from the discharge conveyor 14 under the operation of gravity in the form of a waterfall off of the end 36, or nose, of the conveyor 14 and can be transported to the shuttle assemblies 20. An optional adjustable side shift mechanism can be incorporated to keep the cheese evenly distributed within the shuttle assembly 20.

The shuttle assembly 20, or receiving receptacle assembly, can receive the cheese shreds 28 as they fall off of or are conveyed off the end 36 of the discharge conveyor 14, where the cheese can be evenly distributed throughout receiving receptacles 22 of the shuttle assembly 20 as they are collected therein. The shuttle assembly 20 can have a plurality of closed or partially closed receiving receptacles or cells 22, from one to greater than one, aligned in a downstream direction for receiving the food products, or cheese shreds 28, from the discharge conveyor 14. In the aspect shown in the figures, eight receiving receptacles 22 are provided in the shuttle assembly 20. The number of receiving receptacles 22 provided can depend upon the number of trays that are filled with the cheese shreds 28 at the same time. Thus, when eight receiving receptacles 22 are provided there can be eight trays 30 or packages that can receive the metered volume of cheese shreds 28 in the tray 30 or in a respective compartment 32 of the tray 30, such as in the cheese compartment of the tray. Where the tray 30 for filling contains multiple compartments 32, only one compartment may receive a volume of cheese. In another aspect, more than one compartment of a multi-compartment tray can receive a volume of cheese, thus, where eight receiving receptacles 22 are filled with cheese there typically will be eight compartments 32 or eight trays 30 that can receive a volume of cheese shreds 28, where the compartments 32 may be from the same or different trays 30.

Each receiving receptacle 22 of the shuttle assembly 20 can have a funnel-like shape and can be mounted on a translating shuttle, such that a timing belt/servo drive can cause the shuttle to move in a translating motion that can actuate the shuttle causing it to move back and forth in the downstream and upstream directions. The receiving receptacles 22 can each include at least one pair of opposing, inclined sidewalls extending between a wider top portion 38 and a narrower bottom portion 40 of the receptacles 22. The receiving receptacles 22 can be mounted in a 4×2 pattern, for example, such that there are four receiving receptacles aligned in a machine direction with two rows deep in a direction transverse to the machine direction. In other words, the receptacles 22 can have a length in the downstream direction greater than a width transverse to the downstream direction. Alternatively, any other number of receiving receptacles can be provided, such as a shuttle 20 comprising at least four receiving receptacles 22. In one aspect, the shuttle 20 can comprise an upstream receptacle, a downstream receptacle, and at least one intervening receptacle aligned in a downstream direction, such that there are at least three receptacles aligned in a machine direction. In another aspect, the shuttle can have at least two receiving receptacles where each receiving receptacle can receive a substantially similar volume of product deposited during the transfer process. In one aspect, the top openings 38 of the receiving receptacles 22 can be rectangular, with a cross machine dimension (i.e., width) of approximately 6 inches, such that all of the receptacles 22 are symmetrical. However, the dimension of the receptacles 22 can be dependent on the conveyor width. Therefore, in another aspect, where the conveyor is about 11 inches wide and the receptacles 22 are mounted in 4×2 pattern, the cross machine dimension or width can be approximately 5.75 inches to about 6.25 inches. Alternatively, any other appropriate shape or dimensions may be provided. Still alternatively, the dimensions of the receptacles can be non-symmetrical such that the first and second receptacle can have a different width or length, for example, or any other arrangement.

The lower openings 40 or bottom end of the receiving receptacles 22 can be round and can taper in size, such that the top opening 38 is larger in size than the bottom opening, like a funnel. In one aspect, the lower end 40 can have about a 1¾ inch inside diameter. However, the lower end diameter can be dependent on the size of the receptacles 22 at the upper end, or top opening 38, such that the lower end can typically be about 1/16 inch to about 1/8 inch smaller than the top of the receptacles 22. Alternatively, any appropriate shape of the lower opening 40 may be provided.

The shuttle assembly 20 can pass the receiving receptacles 22 beneath the shredded cheese waterfalls at the end 36 of the conveyors 14 at the appropriate time and linear speed to fill each of the receiving receptacles 22 with the target metered volume or the target portion weight. The shuttle 20 can travel at a shuttle/receptacle speed or second speed in a downstream direction from a first upstream position, indicated in FIGS. 2A and 2B, at least partially beneath the discharge conveyor 14 to a second, downstream position, indicated in FIGS. 4A and 4B. The shuttle 20 can travel in a back and forth motion. Thus, the conveyor 14 can be travelling at a first speed, or discharge speed, and the shuttle 20 can be traveling at a second speed, or shuttle speed, while the shuttle 20 simultaneously collects the cheese shreds 28 as they are transported off of the end of the conveyor 14. In one aspect, the discharge speed can be less than the shuttle speed. Alternatively, the shuttle 20 can be provided in a looped or "race-track" configuration in which the shuttle 20 can be moving along a circular or elliptical path around a closed loop, such that its movement can be continuous.

Optionally, a divider or guide can be placed at the end of the discharge conveyor 14, such that the cheese shreds 28 or other food product will first contact the divider upon being transported off of the end of the conveyor 14. In one aspect, the divider can have a rectangular shape such that when the food product falls off the end of the conveyor 14 it first contacts the apex or point of the triangular-shaped divider. The divider can help to divide the food product stream falling from the conveyor 14 into two streams to correlate to the two rows of the receiving receptacles 22. Any appropriate shape of the divider can be used.

Once each receiving receptacle 22 has received its respective volume of cheese shreds 28, the shuttle assembly 20 can be paused in the second, downstream position so that each receiving receptacle 22 can discharge its contents into a compartment 32 of a tray 30 positioned beneath the shuttle assembly 20. Each of the receiving receptacles 22 of the shuttle assembly 20 can have a selectively openable portion or moveable gate 34 that can be activated to open and close to drop the cheese 28 into the tray 30. While the shuttle 20 is receiving shreds 28 from the discharge conveyor 14, the selectively openable door 34 can be in the closed state. In one aspect, the moveable gate 34 can be a pivotable door or gate that can be positioned such that it clears a funnel assembly 24 beneath it, discussed in further detail below. The moveable gate 34 can be positioned at an offset pivot, such that it also moves out of the way of the end of the receiving receptacle 22 far enough to allow the cheese to fall without interference from the opened gate 34.

Additionally, a funnel assembly 24 can be provided between the shuttle assembly 20 and a container conveyor 46 for positioning at least one container or tray 30 thereon. The container conveyor 46 can help to position at least one tray 30 beneath the shuttle 20 when in the second position for receiving the cheese shreds 28 from the receiving receptacles 22 and into the tray 30 when the receptacles 22 are opened. The container conveyor 46 can be conveyed in a crosswise direction, as indicated by arrow A, transverse to the downstream machine direction of the portioning assembly 10. The funnel assembly 24 can help guide the cheese shreds 28 into their respective compartment 32, such that the shreds 28 are directed towards their respective compartment 32 with minimal spilling of cheese into adjacent, non-cheese compartments or into adjacent cheese compartments that receive a volume of cheese from a different receiving receptacle 22. The funnel assembly 24 can contain a plurality of hollow funnels 26, and in one aspect, the number of individual funnels 26 can equal the number of receiving receptacles 22 on the shuttle assembly 20 so that each volume of cheese shreds 28 collected in its respective receiving receptacle 22 can have its respective funnel 26 to pass through. The opening or dimension of the funnel can be at least slightly larger than the end of the receiving receptacle 22 to catch all or almost all of the falling cheese from the receptacle 22. In one aspect, the funnels 26 can be cylindrical in shape and can open on both ends, although any shape can be provided as well as providing funnels 24 with doors or gates at either or both ends. In one aspect, each funnel can be aligned with a respective one of the receiving receptacles 22 when the shuttle 20 is in its second downstream position.

In one aspect, the funnels 26 can be actuated to move vertically down and up, such that the top opening 44 of the funnel 26 can be moved down a distance that can clear the discharge end 40 of the receiving receptacle 22 and, in particular, can clear the gate 34 as it is opened. The funnel 26 can also actuate downward to move its lower end 42 into position closer to the tray 30 such that the cheese shreds 28 are closer to the tray 30 upon discharge from the funnel 26 and have less distance to fall. The plurality of funnels 26 can direct the food products from the receiving receptacles 22 into a container 30 positioned on the container conveyor 46, or some other surface, when the receiving receptacles are opened. In another aspect, the plurality of funnels 26 can be provided between the container conveyor 46 and the receiving receptacles of the shuttle, when the shuttle is in the second position.

After the cheese shreds 28 have been deposited from the receiving receptacles 22 into the container or tray 30, the shuttle assembly 20 can then travel in an upstream direction to return to the first position at least partially beneath the discharge conveyor 14. During this time that the shuttle 20 is returning to the first position, the discharge conveyor 14 remains paused. The discharge conveyor 14 can be paused from when the shuttle reaches the second position until the shuttle returns to the first position.

Optionally, a controller may be provided that can be operably connected to an actuator controlling movement of the shuttle 20, such as a timing belt/servo drive, and to a motor controlling movement of the discharge conveyor 14. The controller can be programmed to coordinate operation of the shuttle 20 and discharge conveyor 14 such that the discharge conveyor 14 can be paused during at least a portion of the time interval during which the shuttle 20 is paused and during at least a portion of the time interval during which the shuttle 20 moves in an upstream direction from the second, downstream position to the first, upstream position.

Any appropriate volume or weight of cheese can be collected within the shuttle 20 such that the size of the receiving receptacles 22 of the shuttle 20 are chosen to accommodate the desired volume. In one aspect, the amount of cheese can vary from about 0.50 ounces to 1.5 ounces, for example. In another aspect, the amount of cheese can vary from about 0.50 oz. to about 1.25 oz.

The method of transporting and depositing a metered volume of food product, such as cheese shreds 28 for example, into a compartment of a tray, is shown in FIGS. 2A-5. The pre-shredded cheese (shredding process not shown) can be loaded by a hopper or manually onto a loading conveyor 12. The cheese shreds 28 on the loading conveyor 12 can be advanced toward a discharge conveyor 14. The advancement of the loading conveyor 12 can be controlled by an optional sensor, as discussed previously.

Once the cheese shreds 28 are transferred to the discharge conveyor 14 from the loading conveyor 12, the plurality of cheese shreds 28 can be transported in a downstream direction at the discharge speed. The cheese shreds 28 can be advanced toward the raking system 16, which uses fingers or rakes 18 to evenly distribute the cheese shreds 28, as previously discussed. The cheese shreds 28 continue to advance until they fall from the end 36 of the conveyor 14 under the operation of gravity, as shown in FIGS. 3A and 3B, and into the receiving receptacles 22 of the shuttle assembly 20 below. The advancement of the discharge conveyor 14 can be controlled by a motor that controls movement of the conveyor.

At the start of the fill cycle, the shuttle assembly 20 can be positioned at least partially under the discharge conveyor 14, as seen in FIG. 2B. The shuttle assembly 20 can then be synchronized with the discharge conveyor 14 both starting and stopping at the appropriate time in the filling cycle. The filling cycle can comprise the shuttle assembly 20 being actuated to start accelerating at a second velocity, $V_2$, while the conveyor 14 similarly has started to advance at a first velocity, $V_1$, shown in FIGS. 3A and 3B. The shuttle 20 may begin accelerating at its second velocity, $V_2$, at a slight delay behind the start of acceleration of the discharge conveyor 14. Once the cheese shreds 28 have reached or are about to reach the end 36 of the conveyor 14 the shuttle 20 can begin to accelerate. Thus, the conveyor 14 can begin moving to transport the plurality of cheese shreds 28 at a discharge speed before the shuttle 20 can begins moving and before the step of transferring the plurality of cheese shreds into the shuttle 20. This delay in the start of the shuttle 20 can allow for a first portion of the plurality of cheese shreds 28 to transfer into at least a receiving receptacle 22, and in particular the frontmost receiving receptacle, prior to the shuttle 20 traveling from the first position toward the second position. The shuttle assembly 20 can travel in a machine direction, which is the same direction of travel as the conveyor 14, and can stop once all of its receiving receptacles 22 are filled with cheese. Likewise, the conveyor 14 can also stop once all of the receiving receptacles 22 have been filled. Thus, at the end of the filling cycle, the shuttle assembly 20 can be positioned over the funnel assembly 24, which in turn can be positioned over the trays 30, as shown in FIGS. 4A and 4B.

Therefore, the filling cycle can comprise the back and forth movement of the shuttle, where the shuttle begins advancing in a downstream direction after a set time interval of the discharge conveyor 14 beginning to advance. Once the shuttle 20 reaches the second position, both the discharge conveyor 14 and the shuttle 20 may stop or pause. The discharge conveyor 14 can remain in the stopped or paused state until the shuttle 20 returns to the first position at least partially beneath the conveyor 14. The shuttle 20 can remain in the paused state long enough to open the doors 34 and to deposit the cheese shreds 28 into the trays 30 below. Once the shuttle 20 has completed the transfer of product, then the shuttle 20 can begin moving again, such that it returns to the first position by traveling in an upstream direction. The cycle can then be repeated. If there are no trays 30 in position beneath the shuttle 20 when it is in the second position, then the shuttle 20 may either remain paused in the second position until the trays 30 are in the second position or the shuttle 20 can return to the first position.

Gates or doors 34 can be used to close the lower or bottom openings of each receiving receptacle 22 during the filling process and can open while the shuttle is in the second position located above one or more trays to dispense or transfer the collected volume of cheese into the trays 30 at the end of the filling cycle. The one or more trays 30 can be aligned below the shuttle 20 in the second downstream position. The trays 30 can either be in a stopped position, beneath the second position of the shuttle 20, or the trays do not have to come to a stopped position at all. For example, the trays 30 can be moving slowly beneath the shuttle 20 such that the movement of the trays 30 can be timed to position directly beneath the shuttle 20 as it deposits the cheese. Optionally, a sensor can be provided to detect whether a tray 30 is missing, and if a tray 30 is missing then the sensor can provide a message to a gate controller that controls the opening of the gates 34 to keep the gate door 34 closed. Thus, cheese can be prevented from being released from the receiving receptacle 22 when there is no tray 30 to receive it.

Once the gates 34 open to drop the cheese 28 from the receiving receptacle 22 into the tray 30, the cheese can first pass through the funnel 26. The funnel assembly 24 can accept the shredded cheese 28 dispensed from the cell 22 above it and direct the volume of cheese 28 into the tray compartment 32 below it. The funnel 26 can also be actuated to travel along a vertical axis such that upon receiving the shreds 28, the funnel 26 can move vertically downward, in a direction toward the tray 30, such that its discharge end 42, or lower end, is closer to the tray compartment 32, and can move vertically upward again to be back in position. The plurality of funnels 26 can be actuated as the receiving receptacles 22 open to transfer the cheese shreds 28 therethrough before being deposited into one or more trays 30.

The method of metering the cheese shreds or any other flowable food product into a plurality of portions for depositing into a tray or container can comprise, in another aspect, spreading the flowable product into a streaming layer and dividing the streaming layer into a plurality of generally parallel, discrete streams. Each of the discrete streams can be divided into a series of portions that can be moved into alignment with a respective tray. Each of the portions can then be deposited into a respective aligned tray.

Figure 6:
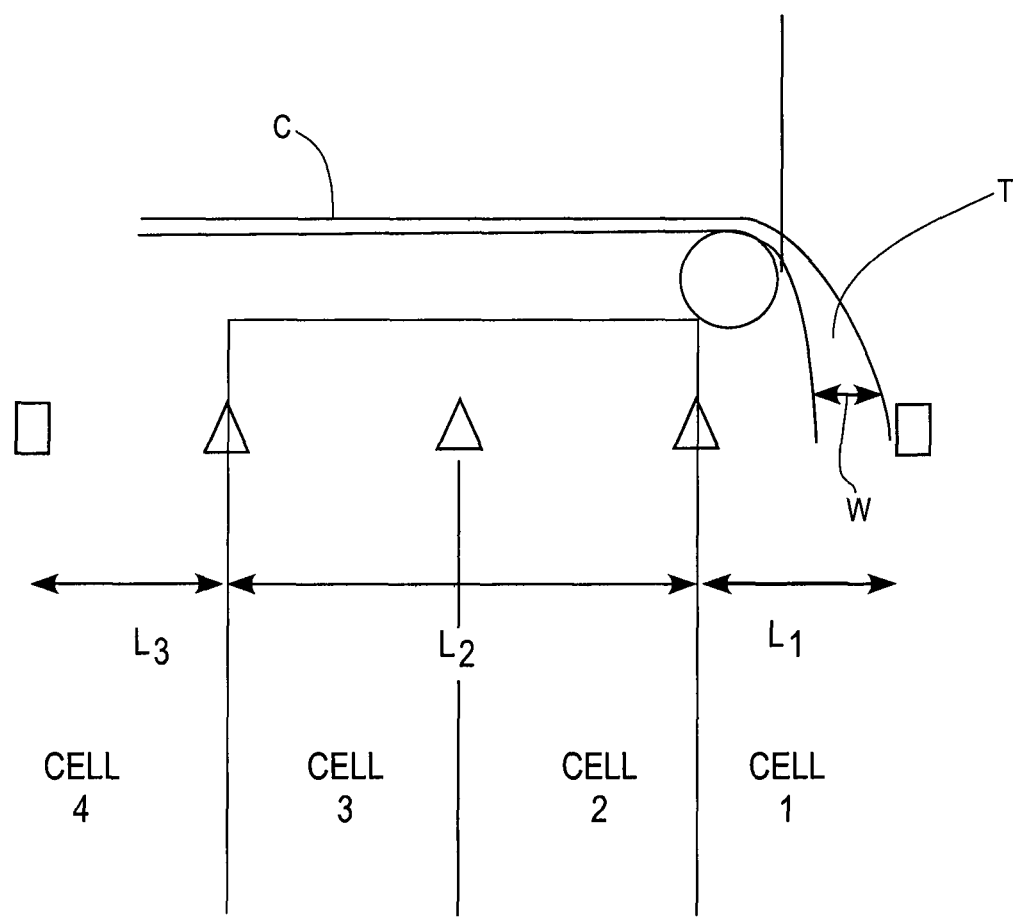
FIG. 6 is a schematic diagram showing the pattern of product falling.

The movement of the shuttle 20 in relation to the movement of the discharge conveyor 14 and the falling cheese can be illustrated by the diagram shown in FIG. 6. Arrow 'c' refers to a layer of cheese on the conveyor spread out at a certain height and width on the conveyor. As the layer of cheese reaches the end of the conveyor, it falls off the end under the operation of gravity. The cheese that falls can fall along a trajectory path, identified as T. The width of the trajectory, T, can be dependent upon a number of factors, one of which can be the height of the layer of cheese upon the conveyor. The higher the height of cheese typically can result in a wider trajectory.

Since a portion of the cheese that falls from the end of the conveyor can fall both along the trajectory path as well as a portion falling vertically down, the first receptacle, or cell 1, can extend beyond the conveyor some distance while in a stopped position. In one aspect, the cell 1 can extend beyond the conveyor at least a distance that is equal to the width of the trajectory of cheese. Thus, since the cell 1 is already partially extending beyond the conveyor, cell 1 does not have to move as far once it begins moving. In one aspect, such as where the shuttle comprises four cells each having a length of six inches, the cell 1 can have a loading distance, $L_1$, of about 5.5 inches, which is the distance or amount of the cell 1 that receives the falling cheese. The remaining 0.50 inches can be used to catch any stray cheese shreds that fall within the outer edges of the trajectory, such as at the frontmost portion of the cell. Thus, the 0.50 inches that catches cheese falling beyond the edge of the conveyor can be at the upstream or front portion of the cell 1. Additionally, the acceleration of the shuttle is occurring at the point in time when cell 1 is being moved.

Cells 2 and 3 are the middle two or intermediate cells and can be moving at the shuttle speed at these points in time, therefore, the loading distance for each is about 6 inches, or whatever the length of the cell is, for a total loading distance, $L_2$, that is equal to the sum of the two cells, or 12 inches in this example.

The final cell, or as shown in FIG. 6, cell 4, can be the cell at which point in time the deceleration is occurring as well as the pausing of the conveyor. Therefore, the loading distance, $L_3$, for this final cell can also be about 5.5 inches because the conveyor is stopping and the flow of cheese is likewise stopping. The loading distance is less than the cell length so that any stray shreds of cheese that may fall off of the end can fall into the remaining 0.50 inches of cell 4 at the downstream end or back end rather than falling outside of the cell walls. By decreasing the loading distance of the last cell a cushion is provided that can catch the stray shreds of cheese that fall off of the stopped conveyor end due to the build-up of momentum and may continue to fall.

Although the first and last cells typically have shorter loading distances than the intermediate cells, the duration of time that the cells are advanced is the same for all.

Figure 7:
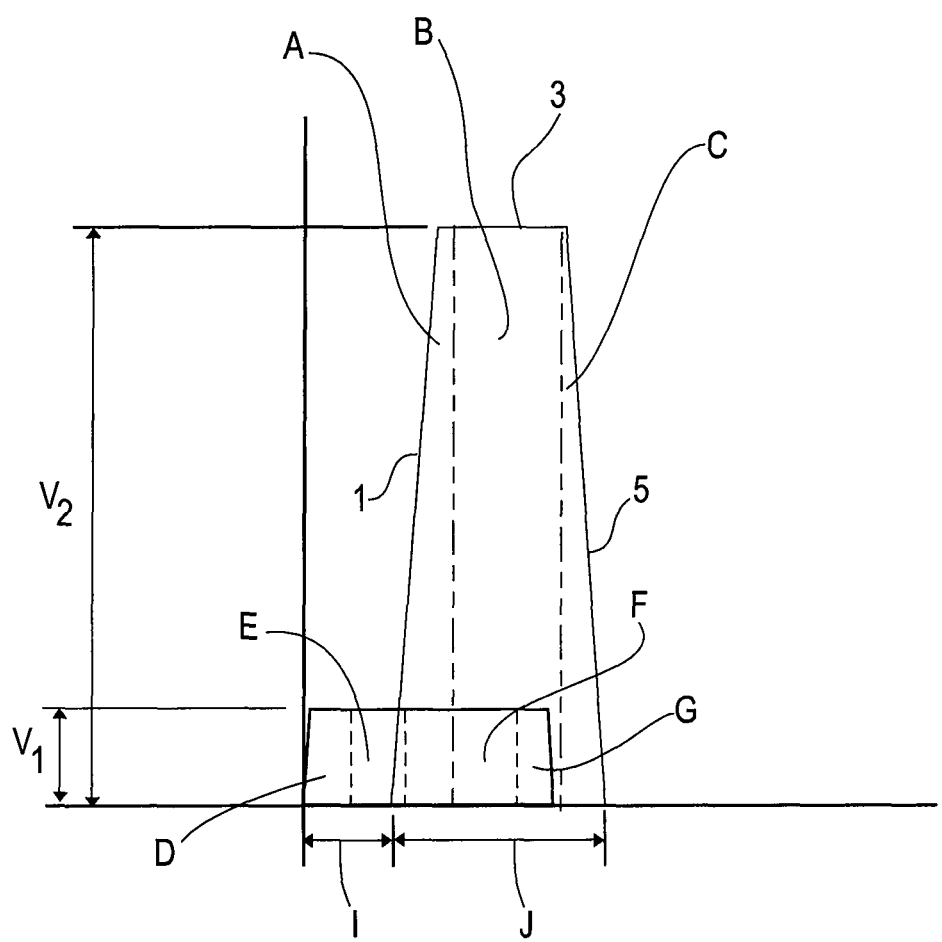
FIG. 7 is a diagram showing the velocity profile for both the shuttle and the conveyor.

An exemplary comparison of a shuttle and conveyor belt velocity profile are illustrated in FIG. 7. References A through C indicate the movement of the shuttle and references D through G indicate the movement of the conveyor belt. Turning to the shuttle velocity profile, line 1 indicates the average acceleration of the shuttle when the cheese has begun to fall (a true velocity profile can have an S-curve profile). The area indicated by letter A can represent the shuttle movement with cheese falling into cell 1, where the shuttle can have four cells as shown in FIG. 6.

Once the shuttle accelerates and reaches the shuttle speed the shuttle travels at a constant speed. This constant speed is shown by line 3, and is equivalent to the shuttle speed $V_2$. The area indicated by letter B can represent the shuttle movement with cheese falling into cells 2 and 3. Finally, the area identified by letter C can represent the shuttle movement with cheese falling into cell 4, as cell 4 decelerates. The deceleration can be shown by line 5.

Additionally, the velocity profile of the conveyor is also shown, where the movement of the conveyor in a downstream machine direction can be shown in four parts. The first part, indicated by letter D, can represent the belt moving before the cheese falls from the end of the conveyor. The second part, shown by letter E, can represent the cheese starting to fall off of the moving conveyor and falling into cell 1. Section F can indicate the cheese falling into cells 2 and 3 where the shuttle has reached its shuttle speed $V_2$ and the conveyor belt has reached its discharge speed, $V_1$. The final section that represents the downstream movement of the conveyor, can be shown by letter G, where the belt can be shown moving with cheese falling from it and into cell 4. After downstream movement of the conveyor shown by letter G, and after transferring the plurality of food products, the conveyor can reverse direction in order to move any food product just on the cusp of falling off the end of the conveyor so that such food product can remain stable on the conveyor and ready for the next sequence of the cycle to repeat.

In one aspect, the entire movement of the conveyor from steps D through G can be carried out in about 1.1 seconds. In the same aspect, the shuttle can have a start delay of about 0.4 seconds after the start of the conveyor belt before the shuttle begins moving. The entire movement of the shuttle from sections A through C can be performed in about 0.93 seconds as indicated by arrow J, for example. It is noted that the movement of the belt can stop before the movement of the shuttle is stopped in order to allow the shuttle to continue to catch and collect any last stray cheese shreds that still may fall off the edge of the stopped conveyor.

In one aspect, the shuttle assembly can be set at a velocity of about 25 in/sec and the discharge conveyor can have a velocity of about 4.167 in/sec. Both can have an acceleration of about 270 in/sec². In the same aspect, the shuttle assembly can advance a distance of about 18.583 inches in about 0.926 sec, while the discharge conveyor can move a distance of about 4.5 inches in about 1.095 sec. Other velocities and parameters are possible.

Although cheese shreds are described herein, any food product appropriate for portioning and depositing into small compartments of a tray or other package can be used instead of cheese. In one aspect, the food products may comprise rice, cookies, crackers, candy, pepperoni, meat, and other appropriate food products.

EXAMPLE 1

The repeatability of filling receiving receptacles 22 of a shuttle assembly 20 with a set amount of cheese was tested. Two different test parameters were chosen. A shuttle assembly 20 was provided having four receiving receptacles 22, where the assembly 20 was moving at a speed of about 22 in/sec with an acceleration and deceleration of about 100 in/sec². The discharge conveyor 14 was traveling at a speed of about 12 in/sec with about 100 in/sec² acceleration and deceleration. The shredded cheese 28 was provided upon the discharge conveyor 14 such that the cheese shreds 28 were assembled to be about 10 inches wide upon the conveyor 14 and having a height of about ¾ inches high. The target weight of cheese collected per cell was about 1 ounce.

Test Run number 1 comprised setting up the discharge conveyor 14 such that the front line or group of cheese shreds 28 were positioned at the end 36 of the conveyor. Upon starting the conveyor, the cheese shreds 28 would then be transported off the end 36 of the conveyor 14 and begin to fall. The shuttle assembly 20 was therefore set to have a delay of about 0.165 seconds after the start of the conveyor 14, with the cheese shreds 28 at the end 36 of the conveyor 14, to allow the shreds 28 to begin their fall. The conveyor 14 and assembly 20 were run during the filling cycle at the designated velocities until the four receiving receptacles 22 were filled with cheese. At the end of the filling cycle, the conveyor 14 and assembly 20 were both stopped and the amount of cheese in each of the four receiving receptacles 22 was weighed, and the deviation from the target weight of 1 ounce was calculated. Test number 1 was repeated a total of four times.

Test Run number 2 was set to a delay of about 0.145 seconds for the shuttle assembly 20 after the start of the conveyor 14 having the shreds at the end of the conveyor 14. All other parameters were kept the same as Test number 1. Test number 2 was repeated a total of three times. Table 1 below shows the results from these tests.

TABLE 1

| Trial No. | Cell No. 1 weight (oz) | Cell No. 2 weight (oz) | Cell No. 3 weight (oz) | Cell No. 4 weight (oz) | Average Weight (oz) | Standard Deviation from Target (oz) |
|---|---|---|---|---|---|---|
| 1-1 | 1.15 | 0.97 | 0.92 | 1 | 1.01 | 0.10 |
| 1-2 | 1.02 | 0.94 | 1.01 | 0.91 | 0.97 | 0.05 |
| 1-3 | 1.03 | 0.96 | 0.97 | 0.91 | 0.97 | 0.05 |
| 1-4 | 1.13 | 0.87 | 0.91 | 0.86 | 0.94 | 0.13 |
| 2-1 | 1.09 | 0.98 | 0.89 | 0.96 | 0.98 | 0.08 |
| 2-2 | 0.94 | 0.93 | 1.04 | 1.06 | 0.99 | 0.07 |
| 2-3 | 0.97 | 0.93 | 1.05 | 0.98 | 0.98 | 0.05 |

A standard deviation of about 0.10 or less was observed with the seven trials that were run. These were considered to be acceptable results as the amount of cheese collected did not vary a great deal and especially did not vary one standard deviation or higher, remaining below one standard deviation.

EXAMPLE 2

The repeatability of filling receiving receptacles 22 of a shuttle assembly 20 with a measured amount of uncooked rice was tested. The rice was employed to provide a food product that remains relatively consistent in weight and density over time such that fluctuations due to the food product itself could be eliminated.

A shuttle assembly 20 was provided having four by two receiving receptacles 22, four a total of eight receiving receptacles 22, such that there are two rows of four receptacles each. The assembly 20 was moving at a speed of about 25 in/sec with an acceleration and deceleration of about 270 in/sec$^2$. The discharge conveyor 14 was traveling at a speed of about 4.44 in/sec. The rice was provided upon the discharge conveyor 14, where the rake speed was provided at 45 RPM, providing a rake height of about 0.75 inches and a bed width of about 10.38 inches. The target weight of rice collected per receiving receptacle was about 2.0 ounces.

The test was run by setting up the discharge conveyor 14 such that the front line or group of rice was positioned at the end 36 of the conveyor. Upon starting the conveyor, the rice would then be conveyed off the end 36 of the conveyor 14 and begin to fall. The shuttle assembly 20 was therefore set to have a delay of about 0.41 seconds before starting after the start of the conveyor 14, with the rice at the end 36 of the conveyor 14, to allow the rice time to begin its fall. The conveyor 14 and assembly 20 were run during the filling cycle at the designated velocities until the four receiving receptacles 22 were filled with rice. At the end of the filling cycle, the conveyor 14 and assembly 20 were both stopped and the amount of rice in each of the four receiving receptacles 22 was weighed, and the deviation from the target weight of 2 ounces was calculated. There were four runs made, which resulted in seven trial results that were collected. The last, or fourth, run only collected rice in one of the two rows of four receptacles. Table 2 provides the weights of rice in each of the four receptacles.

Additionally, the belt segment distances for each receiving receptacle was also measured. Receiving receptacle 1, or the first, frontmost receiving receptacle, traveled a distance of 1.07 in. Receiving receptacles 2 and 3 traveled a combined distance of 2.13 in. Receiving receptacle 4, the final receptacle, traveled a belt distance of 1.07 in.

TABLE 2

| Trial No. | Cell No. 1 weight (oz) | Cell No. 2 weight (oz) | Cell No. 3 weight (oz) | Cell No. 4 weight (oz) | Average Weight (oz) | Standard Deviation from Target (oz) |
|---|---|---|---|---|---|---|
| 3-1 | 1.79 | 2.06 | 2.03 | 2.42 | 2.08 | 0.26 |
| 3-2 | 1.72 | 2.02 | 1.93 | 2.34 | 2.00 | 0.26 |
| 4-1 | 1.74 | 2.08 | 2.01 | 2.43 | 2.07 | 0.28 |
| 4-2 | 1.70 | 2.05 | 1.95 | 2.36 | 2.02 | 0.27 |
| 5-1 | 1.78 | 2.05 | 2.01 | 2.39 | 2.06 | 0.25 |
| 5-2 | 1.74 | 1.97 | 1.94 | 2.30 | 1.99 | 0.23 |
| 6-1 | 1.77 | 2.05 | 1.96 | 2.43 | 2.05 | 0.28 |

A standard deviation of less than about 0.30 was obtained and was considered an acceptable result. These were considered to be acceptable results as the amount of rice collected did not vary a great deal from the target of 2.0 oz. and especially did not vary one standard deviation or higher, remaining below one standard deviation.

What is claimed is:

1. A method of transporting and depositing a metered volume of food product into a container, the method comprising:
    transporting a plurality of food products in a downstream direction at a discharge speed;
    spreading the plurality of food products during the step of transporting the plurality of food products;
    transferring the plurality of food products into at least one closed receiving receptacle, while the receptacle is traveling at a receptacle speed from a first, upstream position toward a second, downstream position;
    aligning one or more containers below the at least one receiving receptacle in the second downstream position;
    stopping the receptacle once it reaches the second position and maintaining the receptacle in a stopped state during a step of opening the at least one receiving receptacle; and
    opening the at least one receiving receptacle while the receptacle is in the second, downstream position to transfer the food products from the at least one receiving receptacle to the one or more containers.

2. The method according to claim 1, wherein the step of transporting a plurality of food products includes using a discharge conveyor, and further comprising pausing the discharge conveyor when the receptacle is in the second position and until the receptacle returns to the first position.

3. The method according to claim 1, wherein the at least one receptacle includes an upstream receptacle, a downstream receptacle and at least one intervening receptacle all aligned in a downstream direction.

4. The method according to claim 1, wherein the discharge speed is less than the receptacle speed.

5. The method according to claim 2, further comprising the step of reversing the discharge conveyor after the step of transferring the plurality of food products.

6. The method according to claim 1, further comprising the step of transferring the plurality of food products off of an end of a discharge conveyor along a trajectory path, the trajectory path having a width, w, and the receptacle extending beyond the end of the discharge conveyor a distance at least equal to the width, w, allowing for a first portion of the plurality of food products to be transferred into a portion of the receptacle extending beyond the end of the conveyor.

7. The method according to claim 1, wherein the step of spreading the plurality of food products further comprises at least one of the steps of leveling the plurality of food products into a relatively uniform layer of stacked products and spreading the plurality of food products into a relatively uniform width extending transverse to a machine direction.

8. The method according to claim 1, wherein the step of transporting a plurality of food products in a downstream direction at the discharge speed begins before the step of transferring the plurality of food products to allow for a first portion of the plurality of food products to be transferred into the receptacle prior to travel of the receptacle from the first position toward the second position.

9. A method of transporting and depositing a metered volume of food product into a container, the method comprising:
    transporting a plurality of food products in a downstream direction at a discharge speed;
    spreading the plurality of food products during the step of transporting the plurality of food products;

transferring the plurality of food products into at least one closed receiving receptacle, while the receptacle is traveling at a receptacle speed from a first, upstream position toward a second, downstream position;

aligning one or more containers below the at least one receiving receptacle in the second downstream position;

opening the at least one receiving receptacle while the receptacle is in the second, downstream position to transfer the food products from the at least one receiving receptacle to the one or more containers; and wherein the step of transporting a plurality of food products includes using a discharge conveyor, and further comprising pausing the discharge conveyor when the receptacle is in the second position and until the receptacle returns to the first position.

10. The method according to claim 9, further comprising the step of reversing the discharge conveyor after the step of transferring the plurality of food products.

11. The method according to claim 9, wherein the at least one receptacle includes an upstream receptacle, a downstream receptacle and at least one intervening receptacle all aligned in a downstream direction.

12. The method according to claim 9, wherein the discharge speed is less than the receptacle speed.

13. The method according to claim 9, further comprising the step of transferring the plurality of food products off of an end of a discharge conveyor along a trajectory path, the trajectory path having a width, w, and the receptacle extending beyond the end of the discharge conveyor a distance at least equal to the width, w, allowing for a first portion of the plurality of food products to be transferred into a portion of the receptacle extending beyond the end of the conveyor.

14. The method according to claim 9, wherein the step of spreading the plurality of food products further comprises at least one of the steps of leveling the plurality of food products into a relatively uniform layer of stacked products and spreading the plurality of food products into a relatively uniform width extending transverse to a machine direction.

15. The method according to claim 9, wherein the step of transporting a plurality of food products in a downstream direction at the discharge speed begins before the step of transferring the plurality of food products to allow for a first portion of the plurality of food products to be transferred into the receptacle prior to travel of the receptacle from the first position toward the second position.

* * * * *